United States Patent [19]
Kruse et al.

[11] Patent Number: 6,006,139
[45] Date of Patent: *Dec. 21, 1999

[54] SINGLE PASS MEDICAL ELECTRICAL LEAD WITH CAP ELECTRODES

[75] Inventors: Ib M. Kruse, Arvika, Sweden; Nicolaas Lokhoff, Kerkgrade, Netherlands; Paulus van Venrooij, Hoensbroek, Netherlands; Arnoldus Bakels, Simpelveld, Netherlands

[73] Assignee: Medtronic, Inc., Minneapolis, Minn.

[*] Notice: This patent is subject to a terminal disclaimer.

[21] Appl. No.: 08/794,402

[22] Filed: Feb. 3, 1997

Related U.S. Application Data

[63] Continuation-in-part of application No. 08/342,976, Nov. 21, 1994, abandoned.

[51] Int. Cl.$^6$ ............................. A61N 1/05; A61B 5/04
[52] U.S. Cl. ....................... 607/125; 607/126; 600/375
[58] Field of Search ................................. 607/119–130; 600/373–375, 381, 382

[56] References Cited

U.S. PATENT DOCUMENTS

| | | |
|---|---|---|
| 3,825,015 | 7/1974 | Berkovits . |
| 3,865,118 | 2/1975 | Bures . |
| 3,903,897 | 9/1975 | Woollons et al. . |

(List continued on next page.)

OTHER PUBLICATIONS

"Orthogonal Electrogram Sensing," Bruce N. Goldreyer, et al., *PACE*, vol.6, Mar.–Apr. 1983, Part II, pp. 464–469.

"Sensing Characteristics of Unipolar and Bipolar Orthogonal Floating Atrial Electrodes: Morphology and Spectral Analysis," Andre E. Aubert et al, *PACE*, vol. 9, May–Jun. 1986, pp.343–359.

"Toward Optimizing the Detection of Atrial Depolarization with Floating Bipolar Electrodes," Robert R. Brownlee, *PACE*, vol. 12, Mar. 1989, pp. 431–442.

"Amplitude and Direction of Atrial Depolarization Using a Multipolar Floating Catheter: Principles for a Single Lead VDD Pacing," Daniel Flammang, et al., *PACE*, vol.14, Jun. 1991, pp. 1040–1048.

"Permanent Pervenous Atrial Sensing and Pacing with a New J–shaped Lead", by Smythe et al., Journal OF Thoracic And Cardiovascular Suygery, 1976, No. 72, pp. 565–570.

"18 Months of Clinical Experience with the Implantable Optimized Sequential Stimulator", by H.D. Funke, World Symposium On Cardiac Pacing, 6TH, Montreal, Quebec, 1979: Montreal Pacesymp., 1979, Chapter 16–3.

"A New Lead for Transvenous Atrial Pacing and Sensing", by Kruse et al., PACE, Jul.–Aug. 1980, vol. 3, pp. 395–405.

"Three–year Clinical Experience with a New Endocardial Screw–In Lead with Introduction Protection for Use in the Atrium and Ventricle", by Bisping et al., PACE, Jul.–Aug. 1980, vol. 3, pp. 424–435.

"'Crown of Thorns'—Single Pass Lead–Clinical Results", by Sowton et al., PACE, Mar.–Apr. 1983, Part II, vol. 6, pp. 470–474.

"Sensing and Pacing with Floating Electrodes in the Right Atrium and Right Atrial Appendage", by Aubert et al., Journal Of Amer. College Of Cardiology, 1987, vol. 9, No. 2, pp. 308–315.

"European Multicenter Prospective Follow–Up Study of 1,002 Implants of a Single Lead VDD Pacing System", by J.C. Pitts Crick, PACE, 1991, vol. 14, pp. 1742–1744.

*Primary Examiner*—Jeffrey R. Jastrzab
*Attorney, Agent, or Firm*—Thomas F. Woods; Harold Patton; Michael J. Jaro

[57] ABSTRACT

The present invention is directed to a single pass medical electrical lead. In one embodiment, the lead features a pair of bipolar electrodes positioned along the lead body so that they are positioned in the ventricle and atrium respectively when the lead is implanted. The lead body features a 90 degree bent reinforced section. The bend has a radius of curvature approximately 13 mm and begins approximately 90 mm from the distal end. This curved section is approximately 40 mm in length when straightened. The ventricular electrodes are positioned approximately 28 mm apart. The bend has at least one tine extending therefrom, an electrode is mounted on the tine.

51 Claims, 15 Drawing Sheets

U.S. PATENT DOCUMENTS

| | | |
|---|---|---|
| 3,911,928 | 10/1975 | Lagergren . |
| 3,935,864 | 2/1976 | Lagergren . |
| 3,949,757 | 4/1976 | Sabel . |
| 4,057,067 | 11/1977 | Lajos . |
| 4,154,247 | 5/1979 | O'Neill . |
| 4,289,144 | 9/1981 | Gilman . |
| 4,328,812 | 5/1982 | Ufford et al. . |
| 4,393,883 | 7/1983 | Smyth et al. . |
| 4,401,126 | 8/1983 | Reenstierna . |
| 4,401,127 | 8/1983 | Littleford . |
| 4,402,328 | 9/1983 | Doring . |
| 4,402,330 | 9/1983 | Lindemans . |
| 4,422,460 | 12/1983 | Pohndorf . |
| 4,444,195 | 4/1984 | Gold . |
| 4,458,677 | 7/1984 | McCorkle, Jr. . |
| 4,493,329 | 1/1985 | Crawford et al. . |
| 4,502,492 | 3/1985 | Bornzin . |
| 4,567,901 | 2/1986 | Harris . |
| 4,627,439 | 12/1986 | Harris . |
| 4,727,877 | 3/1988 | Kallok . |
| 4,882,777 | 11/1989 | Narula . |
| 4,913,147 | 4/1990 | Fahlstrom et al. . |
| 4,962,767 | 10/1990 | Brownlee . |
| 5,133,422 | 7/1992 | Coury et al. . |
| 5,172,694 | 12/1992 | Flammang et al. . |
| 5,273,053 | 12/1993 | Pohndorf . |
| 5,306,263 | 4/1994 | Voda . |
| 5,782,898 | 7/1998 | Dahl et al. .................... 607/119 |

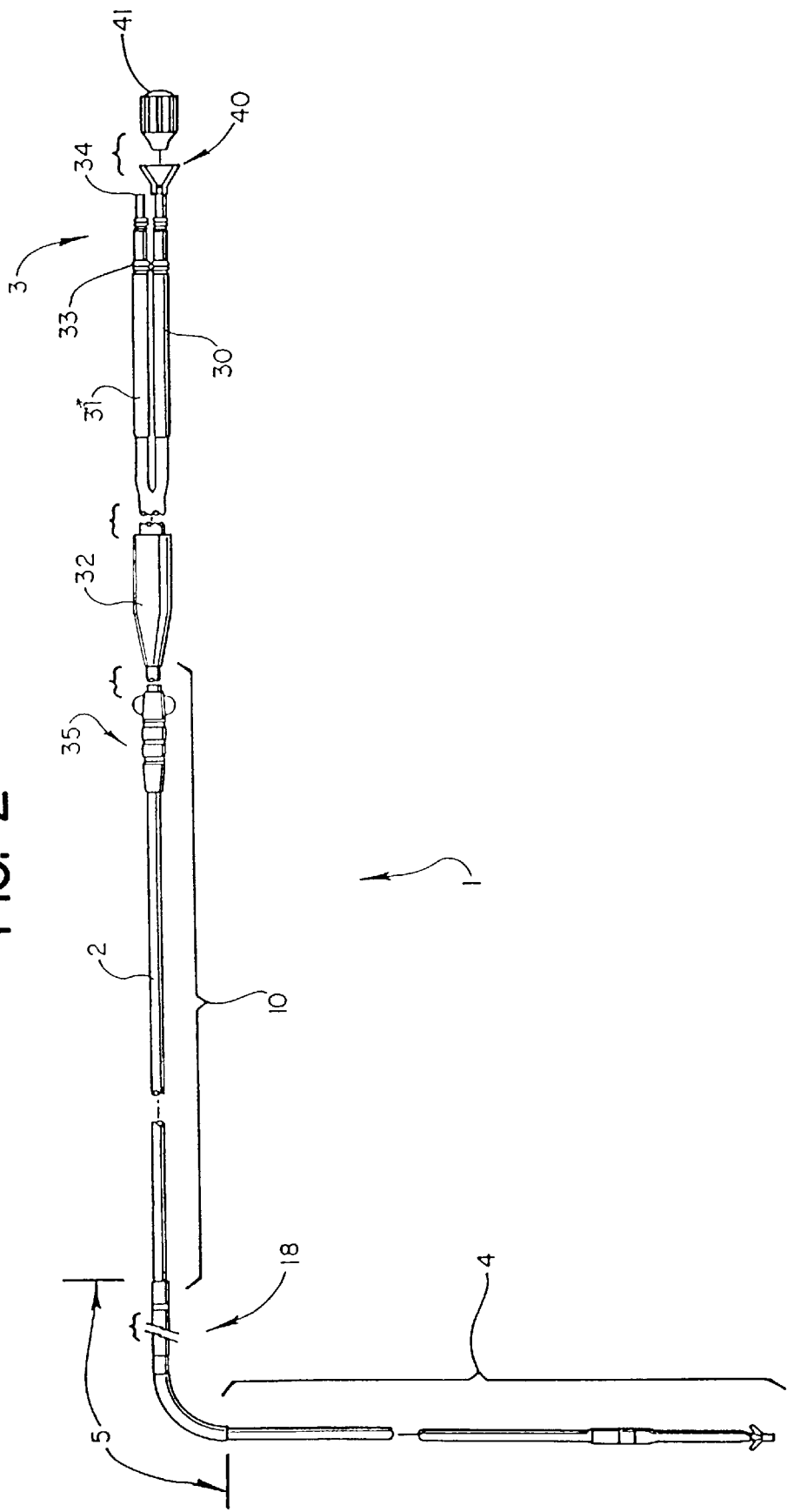

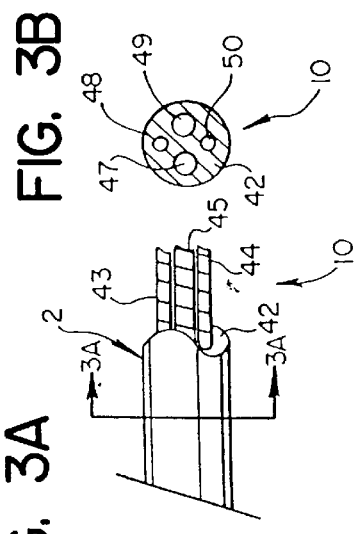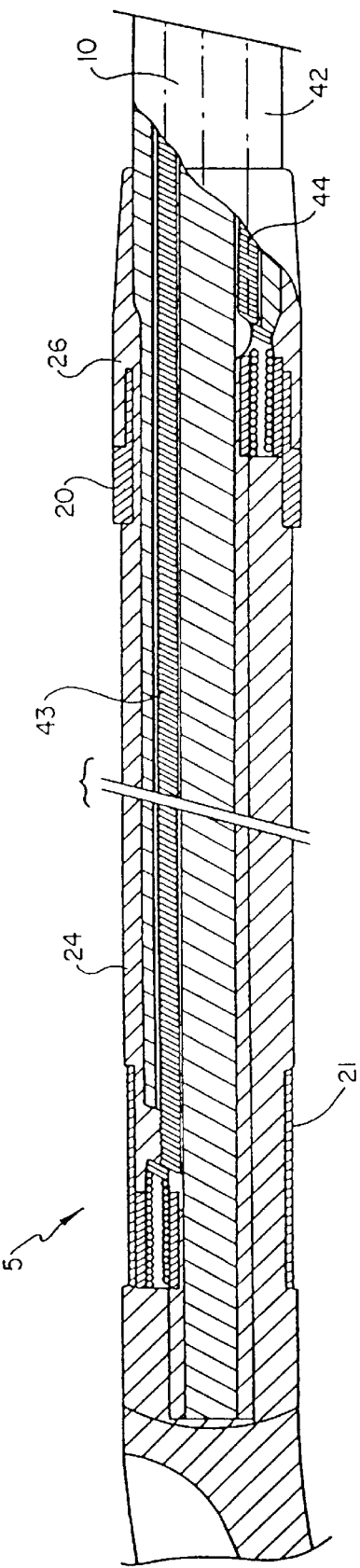

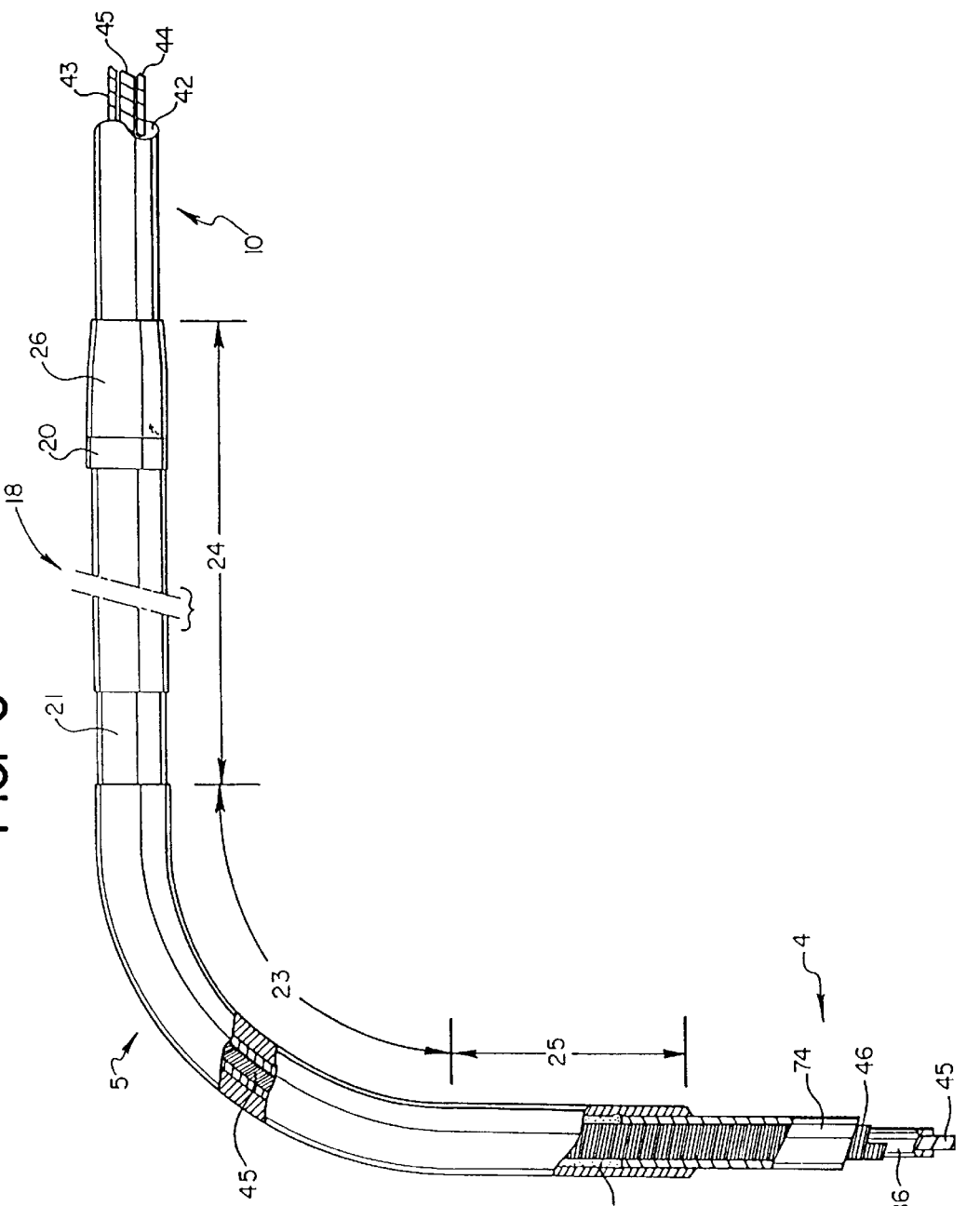

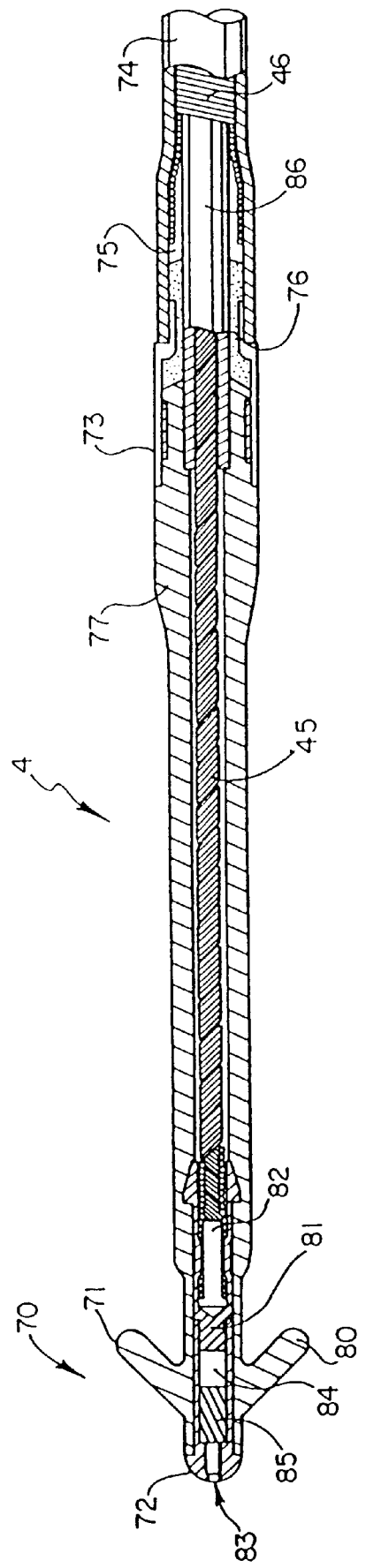

SINGLE PASS MEDICAL ELECTRICAL LEAD WITH CAP ELECTRODES

REFERENCE TO RELATED APPLICATIONS

This is a continuation-in-part of application Ser. No. 08/342,976 "SINGLE PASS MEDICAL ELECTRICAL LEAD" of Kruse et al. filed Nov. 21, 1994, now U.S. Pat. No. 5,628,778.

FIELD OF THE INVENTION

This invention relates to the field of body-implantable medical device systems, and in particular to a body-implantable medical device system which includes a single pass medical electrical lead.

BACKGROUND OF THE INVENTION

Modern electrical therapeutic and diagnostic devices for the heart, such as pacemakers, cardioverters and defibrillators for example, require a reliable electrical connection between the device and a pre-selected region of the heart. Typically an electrical "lead" is used for the desired electrical connection.

One type of commonly used implantable lead is an endocardial lead. Endocardial leads are attached at their proximal end to an implantable pulse generator and at their distal end to the endocardium of a cardiac chamber. Such leads normally take the form of a long, generally straight, flexible, insulated conductor having one end electrically connected to the pulse generator and the other end electrically connected to the endocardium through an electrode. Among the many advantages of an endocardial lead is that it may be positioned into the heart by sliding the lead through a vein until the electrode is properly positioned, rather than physically exposing the heart itself.

The specific design of the endocardial lead used has often varied depending upon the region of the heart to which it is to be connected, in particular whether it is for a ventricular application or an atrial application.

Ventricular endocardial leads are often readily flexible and have tines or fins at their distal end. These tines are provided to engage the trabeculation within the ventricle so as to reliably fix, or at least position, the electrode in the desired location. Unlike the ventricles, the atrial walls are relatively smooth. Because the atrial walls are smooth it has been difficult to retain the electrode in a fixed position with respect to the wall of the atrium. One approach commonly used has been to form the distal end of an atrial lead in a J-shaped configuration. Such a configuration causes the distal end to curve upwardly once the lead is within the atrium so as to provide reliable contact between the electrode and the heart tissue.

In dual chamber pacing, however, it is necessary to establish an electrical connection with both chambers of the heart. Typically this now involves the placement of two leads, a ventricular lead as well as an atrial lead, within the patient's heart. Usually the ventricular lead is placed first, i.e. it is passed through a blood vessel and into the ventricular cavity. When the ventricular pacing lead has been stabilized within the heart, the second lead, or atrial lead, is passed through the blood vessel and is moved into a selected position within the atrial cavity.

The placement of two separate pacing leads into two separate chambers of the heart, however, is a relatively complicated procedure. First as the second lead is being inserted, it is possible to strike the first lead with the second lead thereby dislodging the first lead from its desired position. In addition, the presence of two leads may cause a significant decrease in blood flow through the blood vessel, especially in patients having relatively small diameter vessels. Finally, although transvenous placement of a lead is relatively not traumatic, it would nonetheless be beneficial to simplify and shorten the implant procedure as much as possible. Reducing the number of leads implanted from two to one would be of significant benefit.

Because of the difficulties encountered by placing two leads there has been a considerable number of past attempts to design a single lead which provides an electrical connection to both chambers of the heart, often referred to as a "single pass lead." An early attempt at a single pass lead was taught by Bures in U.S. Pat. No. 3,865,118. Because the configuration taught by Bures requires the ventricular lead to be coaxially mounted within the outer sheath, minimal control could be exercised over placement of the atrial electrodes. To compensate for this lack of control, Bures taught the use of opposing (i.e., spaced by 180 degrees) spring loaded electrodes. Such a placement technique is susceptible to dislodgement, however. It is also electrically inefficient because of the relatively large surface area of the electrode and the difficulty in controlling the amount of that surface area actually in contact with the atrial wall. Furthermore, using the outer catheter to control flexure of the atrial electrodes lead to sealing problems.

Lajos in U.S. Pat. No. 4,057,067 attempted to solve many of the control problems found with the lead taught by Bures by using a "J" shaped atrial lead with stylet control. Because the atrial and ventricular leads, however, were spaced a fixed distance, the lead taught by Lajos did not accommodate various sized hearts. A further problem with the Lajos lead was the establishment of an effective seal of the hole at the distal end of the atrial electrode. During insertion, this hole is blocked by the stylet. Removal of the stylet, however, permitted seepage of blood into the lead.

A third single pass lead configuration was taught by Sabel in U.S. Pat. No. 3,949,757. Sabel used the "J" shaped atrial electrode placement as taught by Lajos but slid the atrial catheter within the outer sheath of the ventricular catheter. This solved one problem of Lajos by not requiring an aperture in the distal end of the atrial electrode for stylet straightening of the "J" shape. It did not completely solve the problem of differing heart sizes, however. The distance between the distal end of the atrial catheter and the distal end of the outer sheath was essentially fixed by practical factors even though the atrial catheter was slidably mounted within outer sheath because sliding of the atrial catheter also changed the shape of the "J". The atrial electrode may be lowered in the atrium by moving the atrial catheter either proximal or distal relative to the outer sheath. However, the atrial electrode may not be raised within the atrium. That distance is effectively established by the prior implantation of the ventricular electrode. Providing a larger distance between the ventricular electrode and the distal end of outer sheath would tend to distort the "J" shape of the atrial catheter.

Another proposed configuration for a single pass lead was disclosed by Gold in U.S. Pat. No. 4,444,195 which disclosed a flexible catheter having a series of ring electrodes selectively utilized for pacing and sensing in both chambers of the heart. As discussed above, one significant problem with this configuration was the reliable, consistent and acceptable placement of the atrial electrodes.

A still further attempt to configure a single pass lead was disclosed by Harris in U.S. Pat. No. 4,627,439 which featured a single pass lead having a prebent atrial section. In particular the atrial section had a bend with the electrodes positioned on the bend. The bend, it was taught would assist in properly maintaining the position of the atrial electrodes. The Harris design, however, failed to provide an acceptable single pass lead. In particular the configuration of the prebent section having electrodes on the bend failed to provide acceptable chronic electrode position.

SUMMARY OF THE INVENTION

The present invention is directed to a single pass medical electrical lead. In one embodiment, the lead features a pair of bipolar electrodes positioned along the lead body so they are positioned in the ventricle and atrium respectively when the lead is implanted. The lead body features a reinforced section preferably having a 90 degree bend. The bend has a radius of curvature approximately 13 mm and begins approximately 90 mm from the distal end. This curved section is approximately 40 mm in length when straightened. The ventricular electrodes are positioned approximately 28 mm apart. The ventricular cathode electrode is positioned at the distal end of the lead. The atrial electrodes are positioned approximately between 5–35 mm apart, with 28 mm preferred. The atrial anode is located at a position immediately adjacent and proximal the 90 degree bent reinforced section.

BRIEF DESCRIPTION OF THE DRAWINGS

The above-described and other aspects of the present invention may be better understood and appreciated with reference to a detailed description of a specific embodiment of the invention, when read in conjunction with the accompanying drawings, wherein:

FIG. 2 is a plan view of the lead;

FIG. 3a and 3b are detailed sectional views of a proximal section of the lead body;

FIG. 5 is a detailed sectional view of the atrial electrode assembly positioned on the reinforced section of the lead;

FIGS. 6 and 7 are detailed sectional views of the reinforced section;

FIG. 10 is a sectional view of the distal section of the lead;

It should be understood the drawings are not necessarily to scale.

DETAILED DESCRIPTION OF THE INVENTION

The present invention is described within the context of a single pass bipolar transvenous endocardial lead adapted for use in connection with an implantable cardiac pulse generator, such as the Medtronic Legend™ or Thera™ as well as other models commercially available from Medtronic, Inc., Minneapolis, Minn. The present invention, however, may be advantageously practiced in conjunction with many different types of implantable medical devices as well as many other various embodiments of therapeutic or diagnostic catheters and is not limited only to medical electrical leads. For purposes of illustration only, however, the present invention is below described in the context of a transvenous endocardial lead.

THE LEAD

Figure 1:
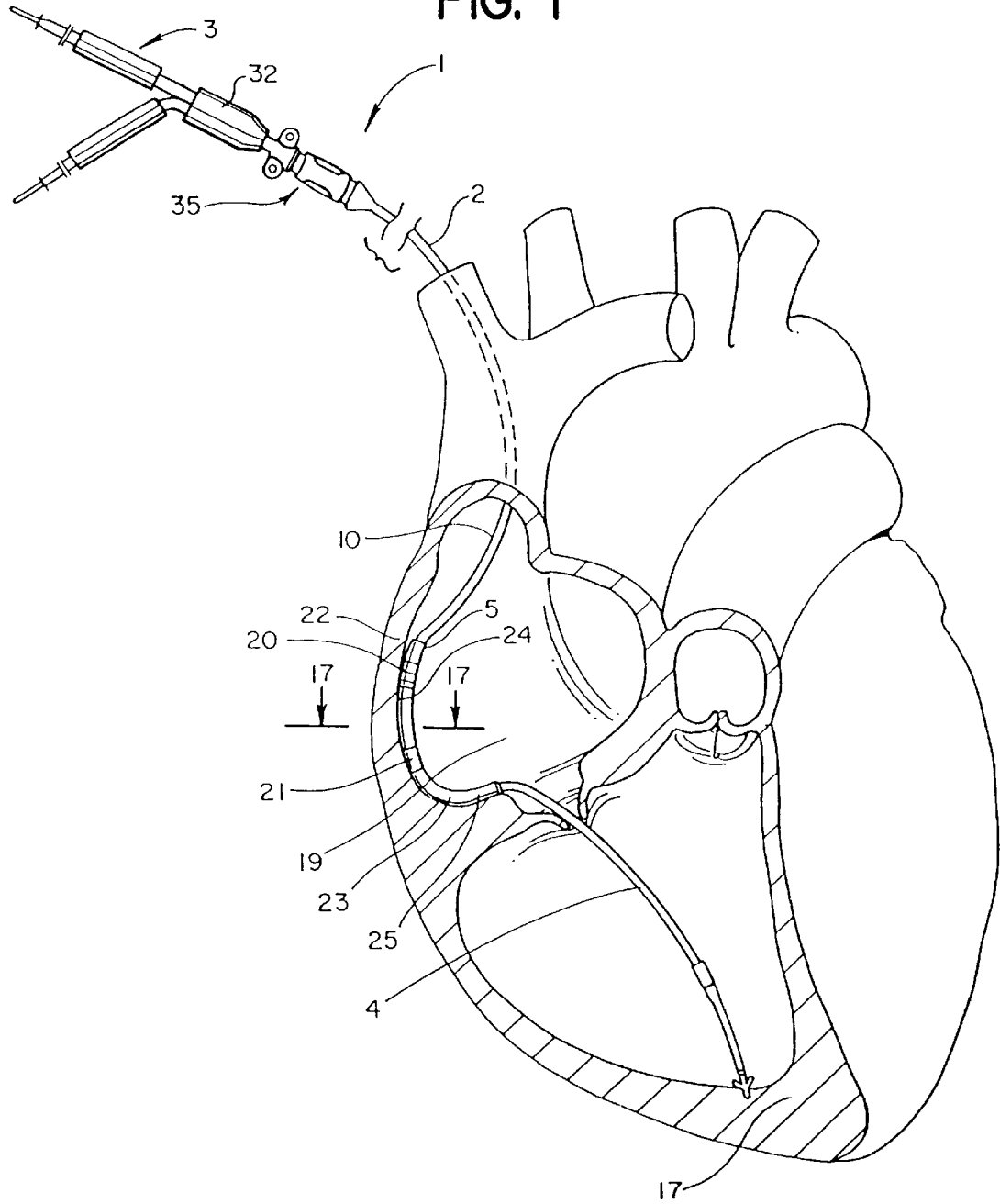
FIG. 1 is a perspective view of the lead implanted in a heart.

FIG. 1 is a perspective view of a lead according to the present invention implanted within a heart. As seen lead 1 consists essentially of a lead body 2 and a connector assembly 3. Lead body 2, in turn, has essentially three sections: a distal section 4, a reinforced section 5 and a proximal section 10. As seen reinforced section 5 has a larger or heavier insulative cover so as to be less flexible or more stiff than either of the other sections and furthermore to have a permanent bend (as best seen in FIG. 2, discussed in detail below.) In a preferred embodiment the permanent bend of reinforced section 5 is between 135 and 45 degrees, where 90 degrees is preferred.

In an alternate embodiment reinforced section 5 has a permanent bend between 135 and 45 degrees along a first plane, between 5 and 90 degrees in a second plane and between 5 and 90 degrees in a third plane. Other degrees of bend the planes may further be used and be within the scope of the present invention.

The flexibility and bend relationship among these sections is important in the present invention because it maintains the atrial electrodes 20, 21 in their desired position. In particular reinforced section 5 essentially functions as a spring to thereby cause the atrial electrodes 20, 21 to contact or be disposed very near atrial wall 22 and thereby provide a suitable electrical connection with the atrial tissue. Reinforced section 5, moreover, is flexible so as to permit the lead body and thus atrial electrode assembly 18 to conform along with the heart as it contracts and, in addition, to be positioned in a specific area of the atrial tissue by adjusting lead 1 at its distal end.

Lead 1 is constructed as follows: A connector pin assembly 3 is positioned at the proximal end of lead body 2, as best seen in FIG. 2. Connector pin assembly 3 features a pair of connector pins 30, 31 electrically connected to lead body 2 by bifurcation 32. Connector pin assembly 3 provides an electrical coupling between lead 1 and an implantable pulse generator (not shown.) Each connector pin 30, 31 has sealing rings 33 and terminal pin 34, all of a type known in the art. In a preferred embodiment each connector pin 30, 31 is constructed to meet the industry standard IS-1 Bi. Furthermore, while in the preferred embodiment a pair of connector pins are provided, a single quadrapolar connector pin may alternatively be used, as is known in the art.

An anchoring sleeve 35 may also be provided for suturing lead body 2 to body tissue. Anchoring sleeve 35 and connector pin assembly 30, 31 are preferably fabricated from silicone rubber, although they may also be constructed of any other suitable biocompatible material known in the art.

One connector pin 30 may also include stylet guide 40 and stylet assembly 41 coupled to terminal pin 34 for imparting stiffness to lead 1 during placement, as discussed in detail below. Stylet guide 40 and stylet assembly 41 are typically discarded after use and before connection of lead 1 to a pacemaker pulse generator (not shown.)

Proximal section 10 of lead body 2 extends from bifurcation 32 to reinforced section 5 and has a length of between 302 mm and 327 mm, where 315 mm is the preferred length.

As best seen in FIG. 3a and 3b which shows sectional fragmented views of proximal section 10 of lead body 2, lead body 2 consists of a quadralumen sleeve 42 having four conductors 43, 44, 45 and 46 (conductor 46 is obstructed by conductor 45 in this particular view) positioned within the respective lumens 47, 48, 49 and 50. Sleeve 42 is preferably constructed from silicone and may be surface treated on its outer surface or its inner surface or both according to the teachings of U.S. Pat. No. 5,133,422 entitled "Radio Frequency Glow Discharge Surface Treatment of Silicone Tubing Used as a Covering For Electrical Leads to Improve Slip Properties Thereof" and U.S. patent application No. 08/239,007, now U.S. Pat. No. 5,593,550 entitled "Plasma Process for Reducing Friction Within the Lumen of Polymeric Tubing" both of which are incorporated herein by reference. Conductors 43–46 are multifilar coils and preferably are constructed from MP35N.

Figure 4:
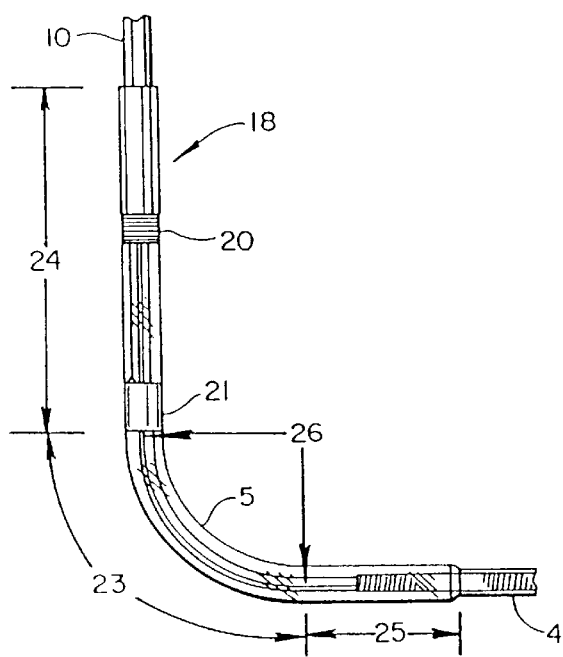
FIG. 4 is a detailed view of the reinforced section of the lead.
Figure 13:
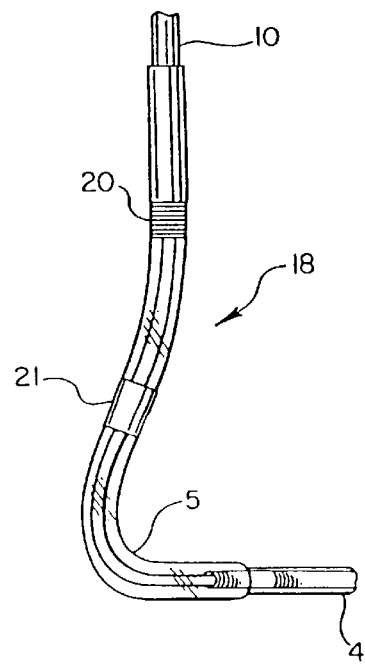
FIG. 13 is a detailed side view of the reinforced section of the lead showing the bend caused by a torque to the proximal end of the lead.
Figure 14:
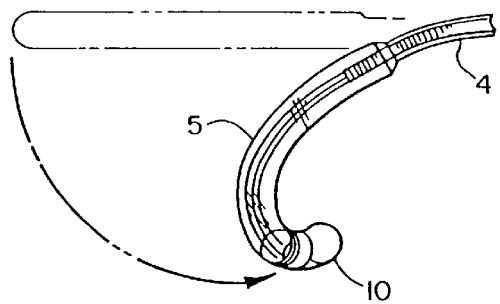
FIG. 14 is a detailed bottom view of the reinforced section of the lead depicted in FIG. 13.

Turning now to the details of reinforced section, FIG. 4 shows reinforced section 5 in whole while FIG. 5 shows a cross-sectional fragmented view of the region of reinforced section 5 where atrial electrode assembly 18 is positioned. As previously discussed above, reinforced section 5 is preferably less flexible than either proximal section 10 or distal section 4 due, in part, to the larger or heavier insulative material used. In the preferred embodiment this material is silicone.

As best seen in FIG. 4 reinforced section has essentially three portions: curved portion 23 having a straight leg portion at either end, viz. proximal straight leg portion 24 and distal straight leg portion 25. Curved portion 23 preferably has a radius of curvature of between 12.5 mm–13.5 mm, with 13 mm preferred, proximal straight leg portion 24 has a length of 38.5 mm–39.5 mm, with 39 mm preferred and distal straight leg portion 25 has a length of between 9.5 mm–10.5 mm with 10 mm preferred. As seen, proximal straight leg section 24 features atrial electrode assembly 18. Atrial electrode assembly 18, in turn, comprises a first electrode 20 and second electrode 21.

In the preferred embodiment first electrode 20 of atrial electrode assembly 18 functions as the cathode and is a whole ring having a surface area of 15 sq. mm. Preferably the ring is constructed of a platinum ring and coated over its external surface with a plating of platinum black as is well known in the art. First electrode 20 further preferably features a helical ridge, as best seen in FIG. 4, to provide better electrical properties, as is well known in the art. See, for example, the U.S. Pat. No. 4,502,492 of Bornzin. Second electrode 21 preferably functions as the anode and is a whole ring of a polished platinum iridium alloy having a surface area of 36 sq mm. In the preferred embodiment first electrode 20 is positioned at the proximal end of proximal straight leg 24 of reinforced section 5. Second electrode 21 is distally positioned from first electrode 20 along proximal straight leg 24 at a distance from first electrode 20 of between 5–35 mm, with 28 mm preferred.

Figure 8:
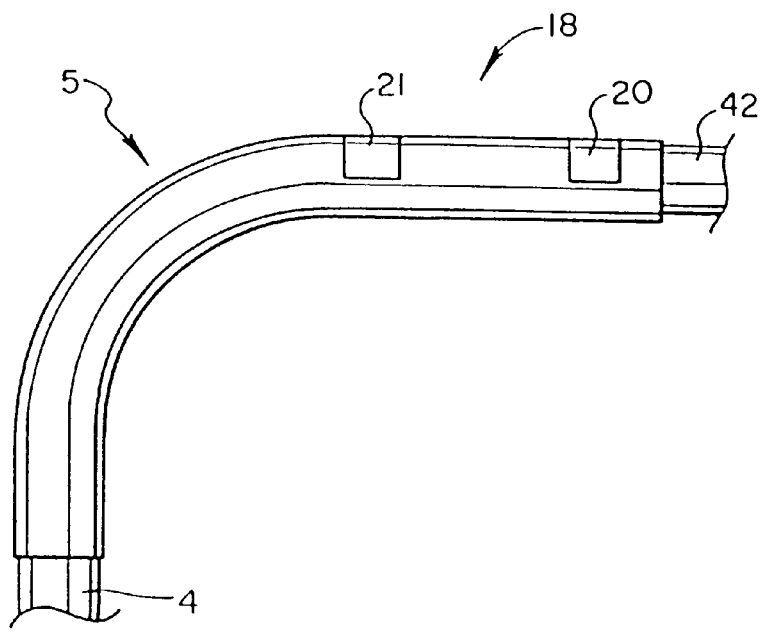
FIGS. 8 and 9A–D depict alternate embodiments of the atrial electrode assembly positioned along the reinforced section of the lead.

FIGS. 6 and 7 provide additional details of the construction of reinforced section 5 and in particular the joining of reinforced section 5 and distal section 4. As best seen in FIG. 7 reinforced section 5, and in particular curved portion 23 and distal straight leg portion 25 has a pair of lumens therethrough in which conductors 45 and 46 run. Conductor 46 has dog leg 51 so that conductors transition from a side by side arrangement to a coaxial arrangement. As seen distal section 4 has conductors 45, 46 arranged coaxially. An additional embodiment of the atrial electrode assembly 18 may be seen in FIG. 8, in which atrial electrodes 20, 21 are half rings rather than whole rings.

Figure 9A:
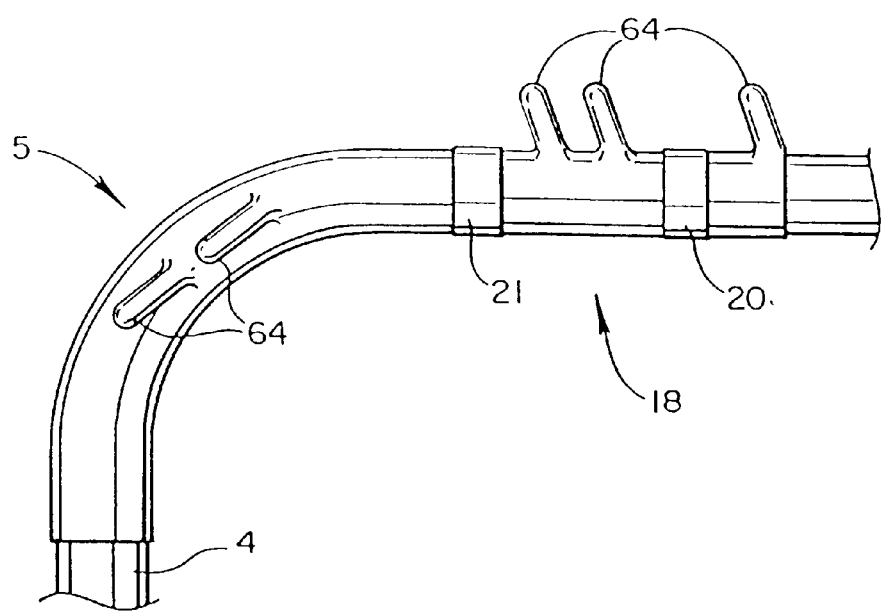

A still further alternate embodiment of atrial electrode assembly 18 of the present invention may be seen in FIG. 9A which discloses providing tines 64 about atrial electrode assembly 18 to permit fixation to atrial tissue.

Figure 9D:
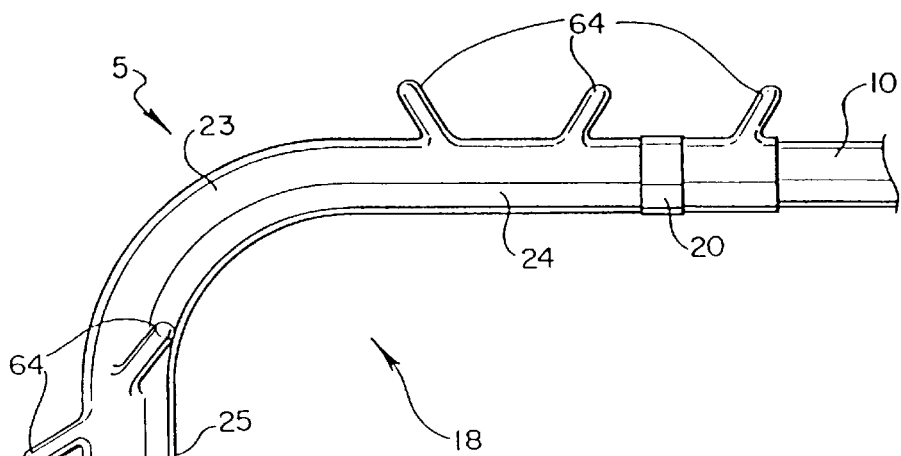
Figure 9B:
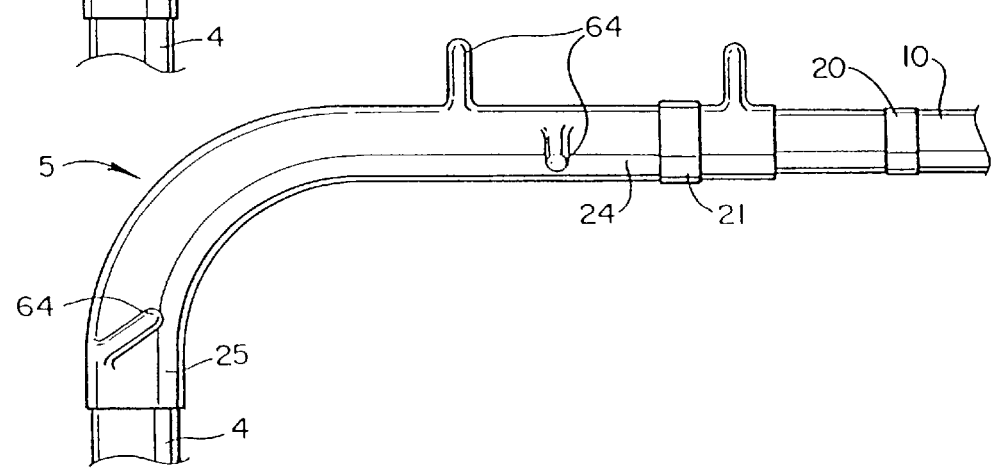
Figure 9C:
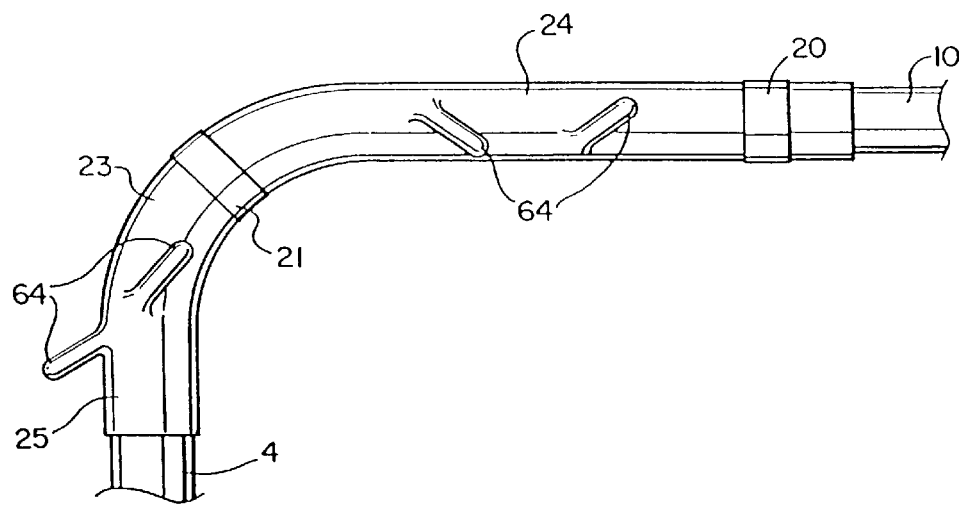

In addition, while the atrial electrode assembly 18 is preferably positioned strictly along straight portion 24 of reinforced section 5, it may additionally be positioned so as to be only partially along reinforced section 5, such as being positioned somewhat more proximal such that first electrode 20 is positioned along proximal section 10 of lead body 2, as seen in FIG. 9B. Likewise atrial electrode assembly 18 may further be positioned so as to be only partially positioned along proximal straight leg portion 24 such that second electrode 21 is positioned along curved portion 23, as seen in FIG. 9C, or positioned along distal straight leg portion 25, as seen in FIG. 9D. Other various configurations and placements of atrial electrode assembly 18 along lead body 2, and in particular with reference to curved portion 23, and proximal straight leg portion 24 and distal straight leg portion 24 of reinforced section 5 may be used and still be within the scope of the present invention. Moreover, as seen, tines 64 may be either slanted in the proximal direction or in the distal direction or both.

Distal section 4 of lead body is connected at the distal end of reinforced section 5 and in particular to the distal end of bent portion 23. Distal section 4 has ventricular electrode assembly 70 mounted thereto and preferably is constructed as is the distal end of the Medtronic Lead Model No. 5024M. As seen in FIG. 10 distal section 4 consists generally of fixation assembly 71 and ventricular electrode assembly 70.

Electrode assembly 70 is, in the disclosed embodiment, of the bipolar type and has tip electrode 72 at its distal end and a ring electrode 73 spaced proximally back from the distal end between 26.7 mm–29.3 mm, with 28 mm preferred. As will be appreciated by those of ordinary skill in the art, tip electrode 72 and ring electrode 73 are coupled to separate, insulated lead conductors.

As best seen in FIG. 7 distal section 4 of lead body 2 has concentric lumens through which the conductors 45, 46 run to tip electrode 72 and ring electrode 73 respectively. As noted earlier conductors 45, 46 are preferably multi filar coils of MP35N or any other suitable alloy such as a platinum-iridium alloy. As seen in FIG. 10, lead body 2 has an outer flexible insulative sheath 74 made from silicone rubber which joins into reinforced section 5 by medical adhesive 88. Outer insulative sheath 74 covers conductor 46. Conductor 46 extends along through lead body 2 and terminates at its distal end where it is electrically coupled, for example by spot or laser welding, to a crimp sleeve 75 made of stainless steel or the like. Crimp sleeve 75, in turn, is in electrical connection with a sleeve 76 which is similarly made of stainless steel or the like. Sleeve 76 is engaged within and in electrical contact with substantially cylindrical ring electrode 73, which is preferably made of a 90/10 platinum/iridium alloy and has a surface area of 36 sq mm.

Partially engaged between ring electrode 73 and tip electrode 72 is a tip/ring spacer 77 made of silicone rubber. Positioned near the distal end of tip/ring spacer 77 are a series of tines 80 as are well know in the art. Conductor 45 is electrically connected to electrode 72 through crimp cylinder 81 and crimp core 82. Thus lumen 47 of conductor 45 extends the length of lead 1, from connector pin 30 to tip electrode 72. As seen electrode 72 has a hole 83 therethrough communicating with hollow 84. Located within hollow 84 is a monolithic controlled release device (MCRD) 85 to dispense a drug, preferably with an anti-inflammatory agent, e.g. a steroid dexamethasone sodium phosphate.

Tip electrode 72 is preferably a porous platinum composition electroplated with platinum black. The porosity, together with the platinum black coating is intended to reduce source impedance and polarization. The porous structure may be made by mixing a conductive material and a binder to form a slurry mixture. The slurry mixture may consist of 70 weight percent of a spherical platinum powder and 30 weight percent of a binder solution. The preferred binder solution consists of 2 percent of an organic binder, such as KLUCELÔ manufactured by Aqualon Corp. of Wilmington, Del. and 98 percent deionized water. This slurry is formed into the desired shape and sintered. Once sintered the porous structure is then preferably electroplated with a material to provide a relatively high microscopic surface area, such as platinum black in the preferred embodiment. Electroplating may be accomplished in any manner suitable so as to deposit a layer of platinum black is deposited over the entire area of the electrode. This produces an electrode having a platinum black surface coating which is sufficiently durable to permit it to be implanted within the body. The porosity, together with the platinum black coating is intended to reduce source impedance and polarization, as is well known in the art.

The steroid also is deposited within the pores of tip electrode 72 as is well known in the art. In a preferred embodiment electrode 72 has a macroscopic surface area of less than 5.8 sq mm. The surface of electrode 72 exposed to the body tissue or fluids or both is generally hemispherical. The small geometric macroscopic electrode size is intended to produce very high pacing impedance. The porous surface configuration together with platinum black electroplating and steroid contribute to a microscopically large surface area for low polarization, low source impedance and low thresholds. The porous surface also facilitates the retention of steroid and adhesion of the platinum black to the electrode surface.

METHOD OF IMPLANTING THE LEAD

Transvenous implantation of lead 1 may be accomplished as follows:

First, lead 1 has stylet assembly 41 inserted through lumen 47 of conductor 45 so the distal end of stylet assembly 41 is adjacent the distal end of lead 1. Stylet assembly 41 is used to impart stiffness to lead 1 and provide steerability, in addition and more importantly, stylet assembly 41 causes lead 1 to straighten bend of reinforced section 5 so lead 1 may be introduced through the venous system. As depicted in FIG. 2 a stylet guide 40 may be temporarily mated over terminal pin 34 of terminal assembly 30 to facilitate the introduction of stylet assembly 41.

Next lead 1 may be introduced into the venous system in any of the ways know in the art, such as through a sub clavian approach. Lead 1 is then pushed through the venous system until tip electrode 72 is positioned within atrium 19.

Stylet assembly is then withdrawn partially from lumen, preferably approximately 10 cm, and lead 1 is continued to be pushed through venous system until tip electrode 72 is positioned proximate ventricular apex 17 and stylet assembly 41 is then withdraw from lumen.

Figures 11, 12:
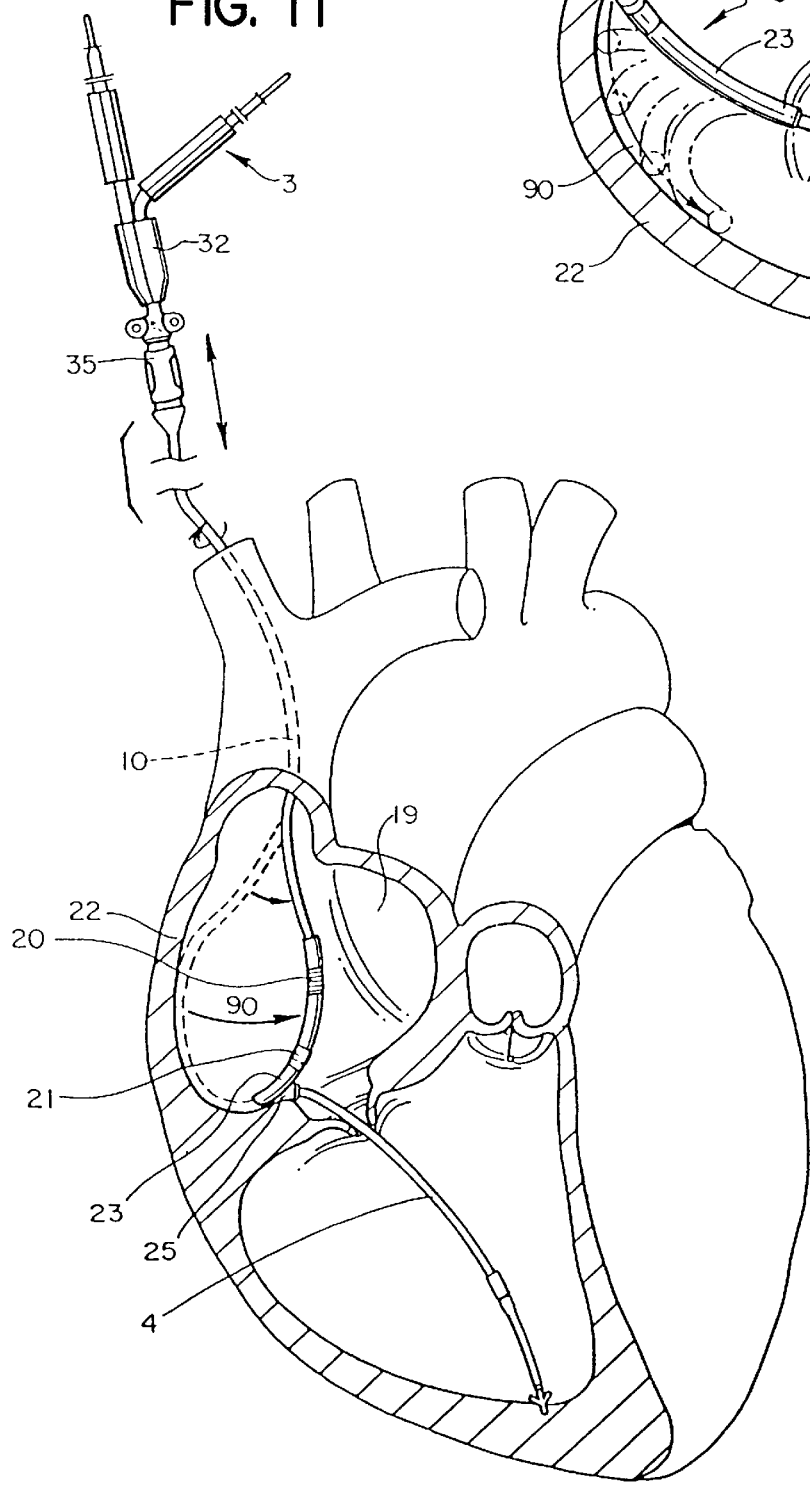
FIGS. 11 and 12 depict the repositioning of the atrial electrode assembly within an atrium of the heart by rotating a proximal end of the lead.

As seen in FIGS. 1, 11 and 12 the unique design of lead 1, and in particular due to the construction, including the relative stiffness, dimensions and shapes of the proximal section 10, reinforced section 5 and distal section 4, once stylet is removed, lead 1 takes a shape such that tip electrode remains positioned at apex 17 while atrial electrode assembly 18 contacts atrial wall 22. Reinforced section 5, although less flexible than proximal section 10 and distal section 4 (distal section 4, in turn is less flexible than proximal section 10) causes atrial electrode assembly to remain in direct contact or extreme close proximity to atrial wall 22. In such a manner atrial tissue may be reliably sensed as well as stimulated through atrial electrode assembly 18.

An additional important feature is depicted in FIGS. 11–14. As seen, rotation of a proximal end of lead 1 in direction 90 causes atrial electrode assembly to move in a path as shown. That is, rotation at proximal end causes atrial electrode assembly 18 to move against or "swipe along" atrial wall 22. This movement permits atrial electrode 18 to be optimally positioned along the atrial tissue, and in addition, to continuously maintain an electrical connection therewith. Besides rotation of the distal end of lead 1, atrial electrode assembly 18 position may also be influenced by the relative amount of lead body inserted into the venous system, that is the amount of lead body distal to the anchor sleeve 35. Thus it is believed a particularly useful anchor sleeve 35 design would be that shown in the U.S. Pat. No. 5,273,053 issued to Pohndorf and entitled "Suture Sleeve with Lead Locking Device."

An important feature of the lead 1, besides allowing the adjustment of the position of the atrial electrode assembly 18 by rotation of proximal end of lead 1 as well as the amount of lead body distal to anchor sleeve 35, is that while this adjustment is occurring the ventricular electrode assembly is not moved and maintains capture. This is due to the relative stiffness and shape of the reinforced section 5 and the position of the atrial electrode assembly 18 thereon.

Figure 15:
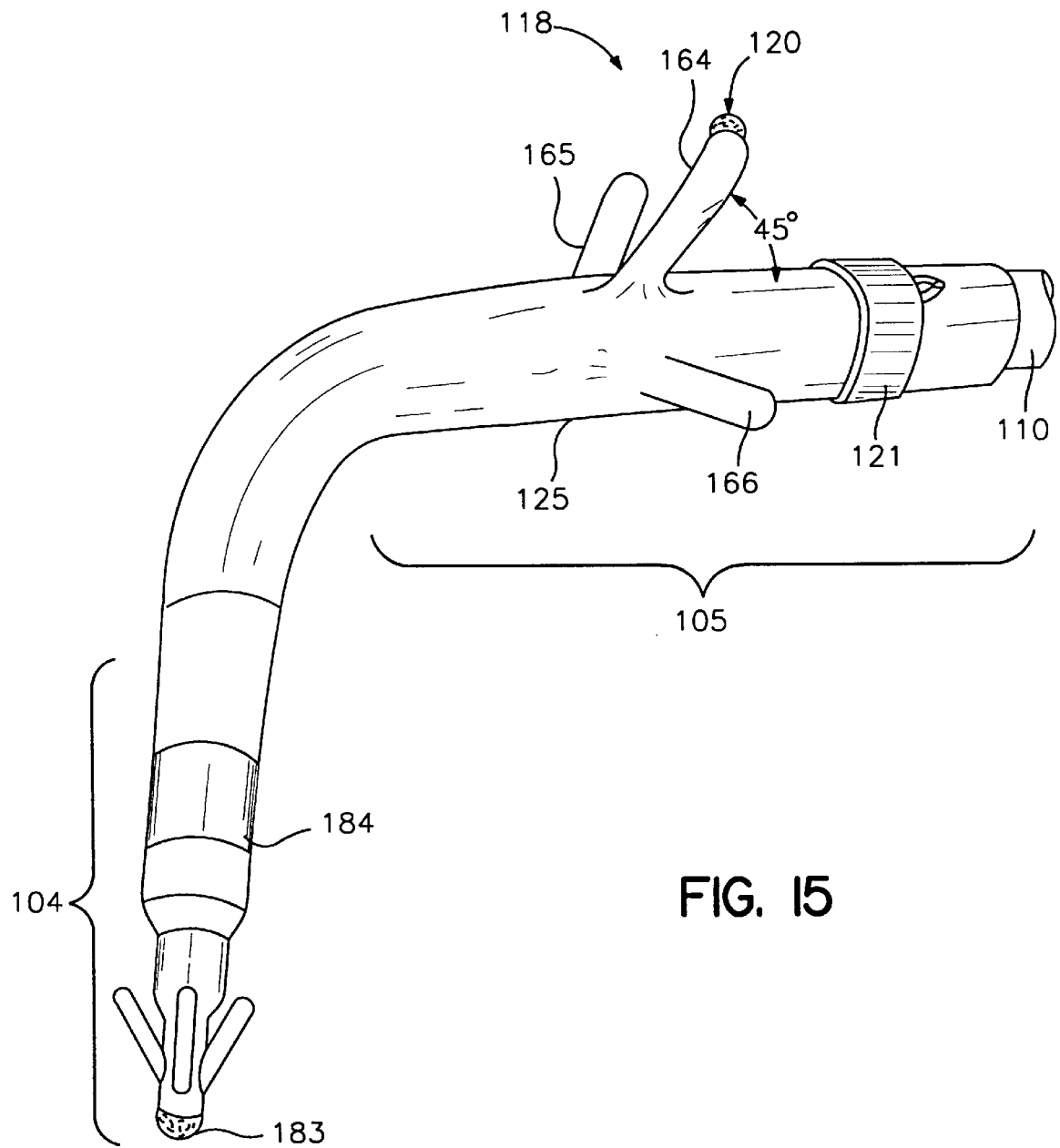
FIG. 15 is an alternate embodiment of the present invention featuring a plurality of tines on the reinforced section, at least one of the tines having an electrode at the tip.

FIG. 15 provides a further alternate embodiment of the present invention. As seen, lead essentially is like those discussed above. That is, as in the other embodiments of the present invention, lead body 102 has essentially three sections: a distal section 104, a reinforced section 105 and a proximal section 110 (only a portion of which is shown in this view). Reinforced section 105 is relatively less flexible or more stiff than proximal section, and proximal section, in turn, is relatively less flexible or more stiff than distal section 104. Moreover, the differing flex characteristics may be accomplished in the same manner as described above, i.e. a larger or heavier insulative cover may be provided along the relevant sections so as to make that section be less flexible or more stiff in comparison to the other sections. Of course other methods to vary the flexibility of the sections may also be used, such as using various conductor configurations and arrangements as well as geometries. In addition a separate stiffening member may also be incorporate within the relevant sections, as shown, for example, in U.S. Pat. No. 4,444,195 to Gold. Besides having a greater stiffness as compared to the other sections, reinforced section 105 also has a permanent bend as seen. Permanent bend is between 45–135° with 90° preferred. All other aspects of this alternative embodiment are similar to those discussed above but for the fact that atrial electrode assembly 118 has a plurality of tines 164, 165, 166.

Figure 16:
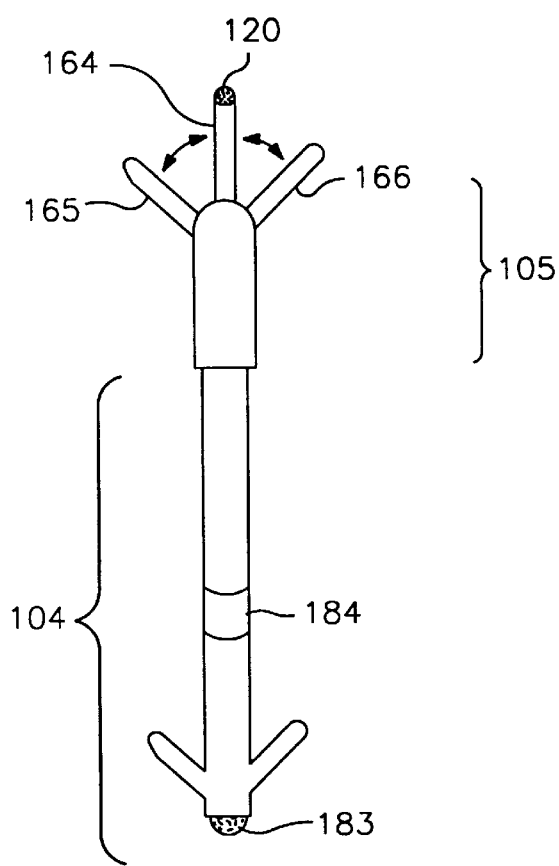
FIG. 16 is a end plan view of the alternate embodiment shown in FIG. 15 showing the orientation of the tines.

In particular, tines 164, 165, 166 are located along proximal straight leg portion 125 of reinforced section 105. Each of tines 164, 165 and 166 are positioned at a 45° angle to the axis of the lead body. Tine 165 is positioned within the plane of the bend of the lead body, as best seen in FIG. 16. Tines 164 and 166, moreover, are positioned at approximately 180° apart with tine 164 positioned approximately midway therebetween, as also seen in FIG. 16. Tine 164 features a first electrode 120. A second electrode 121 is positioned proximal from first electrode 120 along proximal straight leg portion 125 of reinforced section 105, seen only in FIG. 15. First electrode 120 may be of any suitable construction and preferably is constructed using a platinized porous material such as a platinized spherical sintered platinum powder as is well known in the art. Second electrode 121 preferably functions as the anode and is a whole ring of a polished platinum iridium alloy. Distal section 104 is the same as that described above with reference to FIG. 10.

Figure 18:
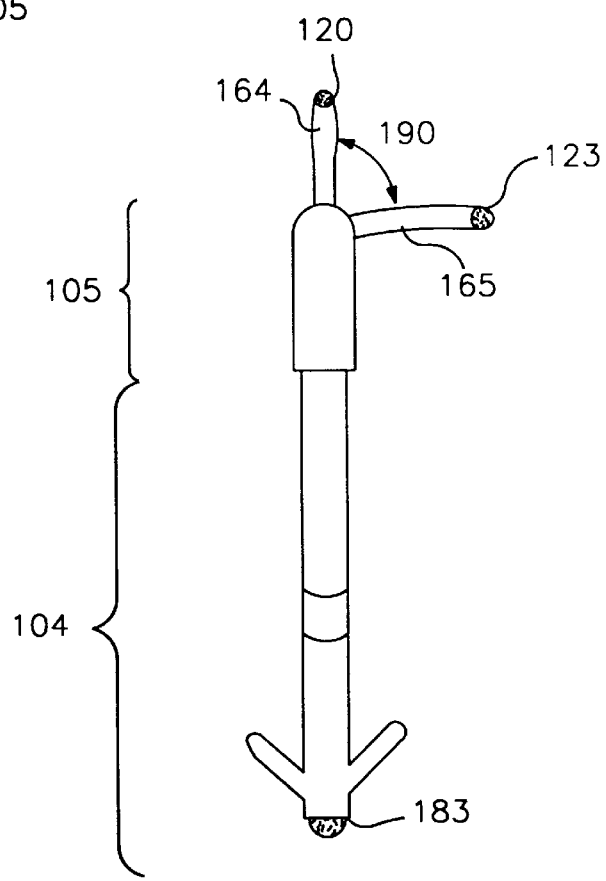
FIG. 18 is a end plan view of the alternate embodiment shown in FIG. 17 showing the orientation of the tines.
Figure 17:
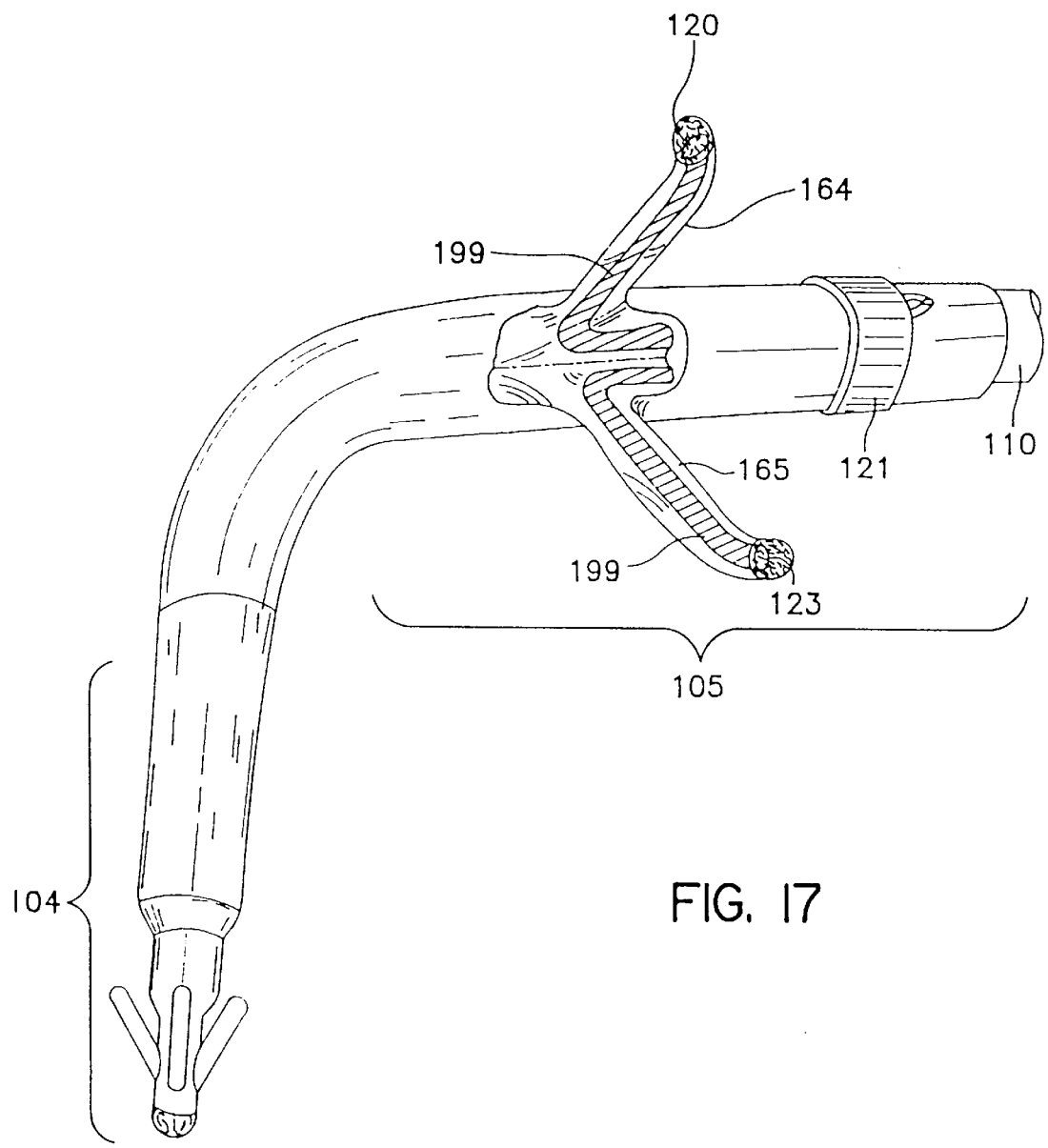
FIG. 17 is an alternate embodiment of the present invention featuring a pair of tines on the reinforced section, the tines having an electrode at the tip.

Turning now to FIG. 17 which shows a still further alternate embodiment of the present invention. As seen, the alternate embodiment of FIG. 17 is substantially similar to that shown in regards to FIG. 15 but for the fact that this alternate embodiment features only a pair of tines 164, 165 positioned along the reinforced section 105. As seen, each tine 164, 165 features electrodes 120, 123 positioned at its tip. Each tine is shown partially cut-away to illustrate the connection of each electrode to a conductor 199. As best seen in FIG. 18, tine 164 is preferably located along the plane of the bend of reinforced section 105 and tine 165 is positioned at an angle 190 thereto, preferably angle 190 is 90°, although other angles may be used.

Figure 19:
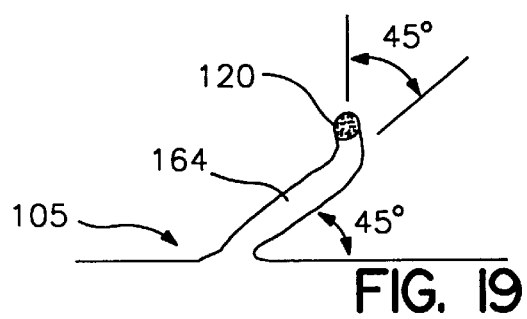
FIG. 19 is a detailed side view showing the orientation of a tine, and the orientation of the electrode on the tine, positioned along the reinforced section.

Turning now to FIG. 19, each electrode on the tip of a tine, moreover, is positioned at an angle to the axis of the tine. As seen, for example, tine 164 positioned along at a 45° to the axis of the reinforced section 105 and has electrode 120 positioned at the tip and canted also at a 45° to the axis of the tine 164. Of course other orientation of the electrode to the tine may be used, such as coaxial to the tine as well as completely perpendicular.

Figure 20:
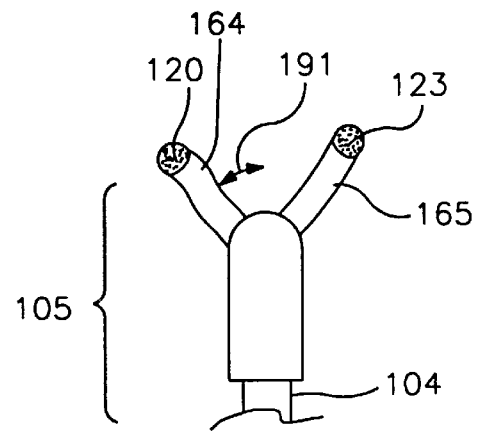
FIG. 20 is a detailed end plan view of an alternate embodiment showning in particular an alternate arrangement for tines posiitoned along the reinforced section.

FIG. 20 depicts a further alternate embodiment for the use of tines having electrodes along reinforced section 105. As seen each tine 164, 165 features electrodes 120, 123 positioned at its tip. Tine 164 is preferably located at an angle 191 relative to the plane of the bend of reinforced section 105 and tine 165 is positioned opposite. Preferably angle 191 is 45°, although other angles may be used. Each electrode may be electrically coupled to an independent conductor and an alternative ring electrode 20 (not shown in this view) may or may not also be used. In the alternative, electrodes 120, 123 may be electrically coupled together.

Figure 21:
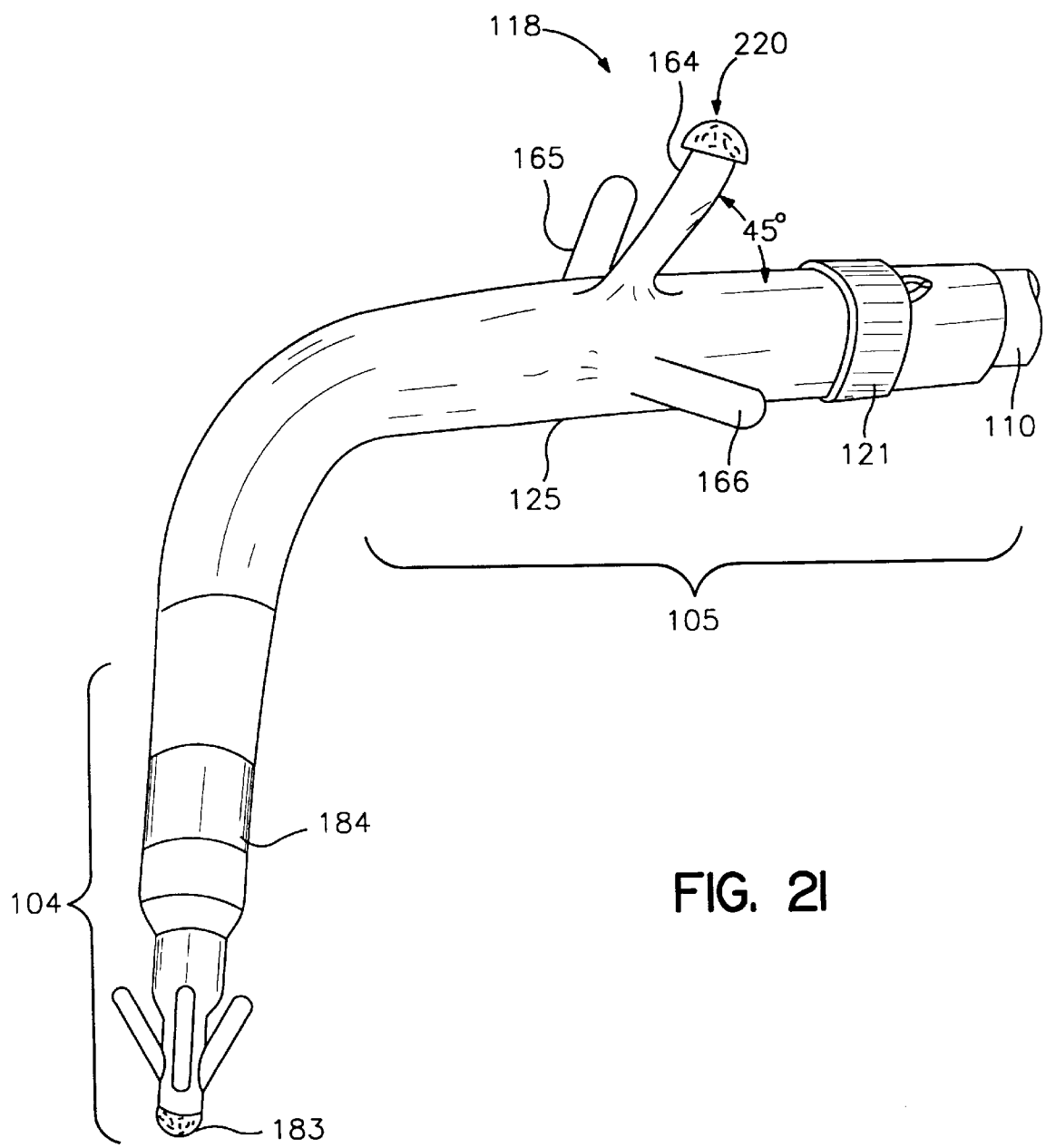
FIG. 21 is a detailed view of an alternate embodiment.

FIG. 21 provides a further alternate embodiment of the present invention. As seen, lead is essentially like those discussed above. That is, as in the other embodiments of the present invention, lead body 102 has essentially three sections: a distal section 104, a reinforced section 105, and a proximal section 110 (only a portion of which is shown in this view). Reinforced section 105 is relatively less flexible or more stiff than proximal section, and proximal section, in turn, is relatively less flexible or more stiff than distal section 104. Moreover, the differing flex characteristics may be accomplished in the same manner as described above, i.e., a larger or heavier insulation cover may be provided along the relevant sections so as to make that particular section less flexible or more stiff in comparison to the other sections. In addition, as also plainly seen in the above description, the use of various conductor configurations will likewise give various stiffness characteristics to each of the lead sections. Of course, other methods to vary the flexibility of the sections may also be used, such as using various conductor configurations and arrangements as well as geometries. In addition, a separate stiffening member may also be incorporated within the relevant sections as shown, for example, in U.S. Pat. No. 4,444,1952 to Gold. Besides having a greater stiffness as compared to the other sections, reinforced section 105 also has a permanent bend as seen. Permanent bend is between 45°–135° with 90° preferred. All other aspects of this alternative embodiment are similar to those discussed above but for the atrial electrode assembly 118.

As seen, atrial electrode assembly 118 features tines 164, 165 and 166. Tine 164 features a first electrode 220. A second electrode 121 is positioned proximal from first electrode 220 on proximal straight leg portion 125 of reinforced section 105. First electrode 220 may be of any suitable construction, and preferably is constructed using a platinized porous material such as a platinized spherical sintered platinum powder as is well known in the art. As discussed above, second electrode 121 preferably functions as the anode and has a whole ring of a polished platinum iridium alloy. Distal section 104 is the same as that described above with reference to FIG. 10.

Figure 22:
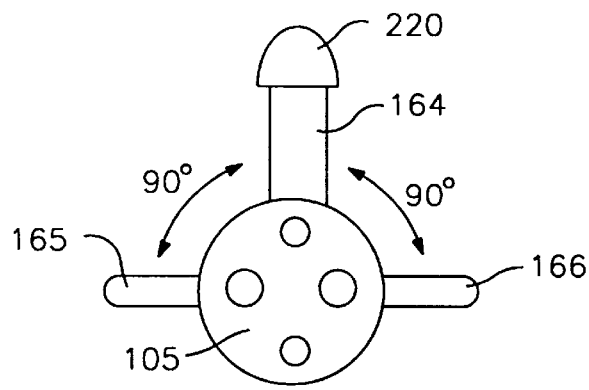
FIG. 22 is a cross sectional view of the embodiment shown in FIG, 21.

Turning now to FIG. 22, which shows an end view of the reinforced section 105 in the area of tines 164, 165, and 166. As seen in this view, tine 164 extends in a relative perpendicular fashion from the axis of reinforced section 105. Tines 165 and 166 further extend in a similar manner at a 90° orientation relative to tine 164. Tines 165 and 166 although shown as extending from a 90° relative away from tine 164 may be oriented in any angular direction relative to tine 164. In fact, it is further conceivable that tines 165 and 166 may be oriented in a parallel manner relative to tine 164.

Figure 23:
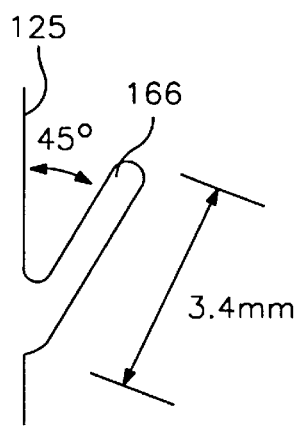
FIG. 23 is a detailed view of a tine extending away from the lead body.

Turning now to FIG. 23 which details the orientation of tine 166 relative to proximal straight leg portion 125 of reinforced section 105. As seen, tine 166 is oriented approximately 45° away from proximal straight leg portion 125 of reinforced section 105. As seen, tine 166 has a length of between 2 and 5 mm with 3.4 mm preferred.

Figure 24:
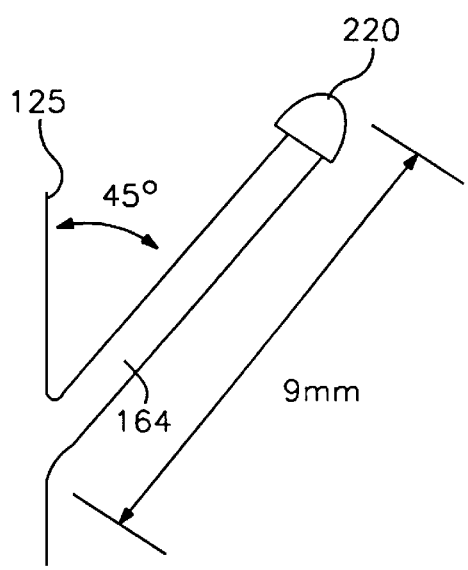
FIG. 24 is a detailed view of a tine having an electrode extending away from the lead body.

Turning now to FIG. 24 which shows a detailed view of tine 164 extending proximal straight leg portion 125 of reinforced section 105. As seen, tine 164 extends between 5 and 15 mm away from straight leg portion, and preferably extends 9 mm away. At the distal end of tine 164 is cap electrode 220. As seen, cap electrode is sized such that it has an overhang or extends about the outer surface of tine 164.

Figure 25:
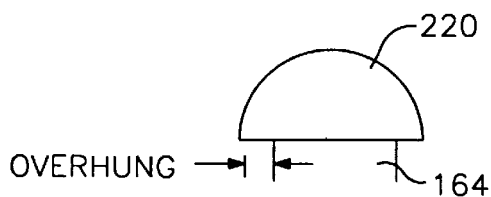
FIG. 25 is a detailed view showing the overhang of the tine electrode relative to the tine.

Turning to FIG. 25, which shows a detailed view of electrode 220. As seen, electrode 220 overhangs the tine 164. Electrode 220 preferably overhangs tine 164 an amount of 0.010 cm–1.000 cm with 0.020 cm preferred. The overhang of cap electrode tine 164 is an important feature of this embodiment as it permits the lead to give excellent sensing and pacing characteristics as compared to the other embodiments where the electrode does not overhang tine 164.

Figure 26:
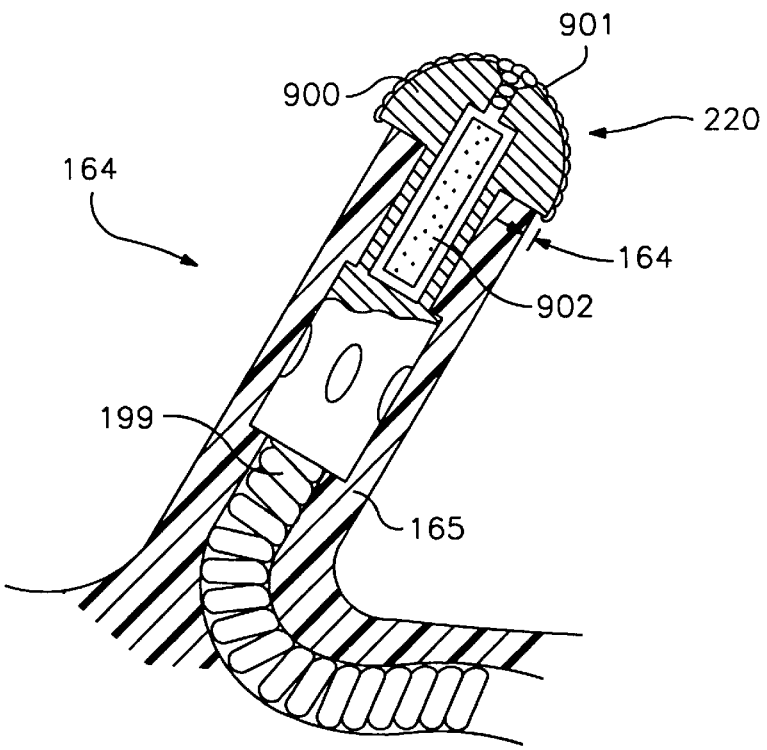
FIG. 26 is a sectional view of a tine and its electrode which elutes a drug.

Turning to FIG. 26, which shows a sectional view of electrode 220. As seen electrode 220 is composed of a solid core 900 coated with a platinized porous material 901. Solid core is preferably a platinum iridium alloy, although other materials may also be used. Porous coating material is the same as that used on tip electrode 183 discussed above. Solid core has a void therein with a lumen or port leading to the porous coating. Mounted within void is a drug eluting device 902, such as an MCRD to elute or dispense a drug, such as a steroid, and more particularly the sodium salt of dexamethasone. Of course other compunds may also be used. Solid core is electrically couple to conductor 199 through a skirt 903 as is well known in the art.

Figure 27:
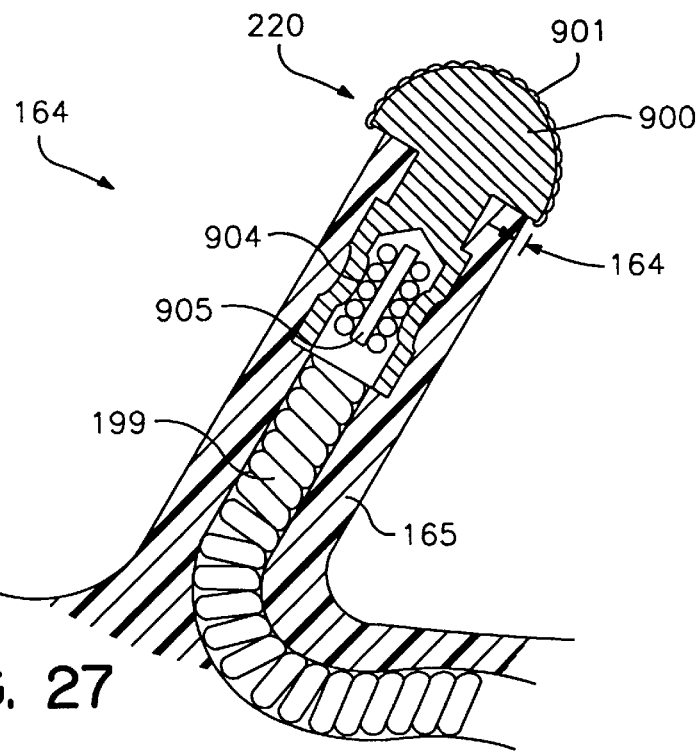
FIG. 27 is a sectional view of an alternate design for a tine and its electrode.

FIG. 27, shows an alternate design of an electrode 220. As seen electrode 220 is composed of a solid core 900 coated with a platinized porous material 901. Solid core is preferably a platinum iridium alloy, although other materials may also be used. Porous coating material is the same as that used on tip electrode 183 discussed above. Solid core is electrically couple to conductor 199 through a crimp 904 and crimp core 905 as is well known in the art.

Although a specific embodiment of the invention has been disclosed, this is done for the purposes of illustration and is not intended to be limiting with regard to the scope of the invention. It is contemplated that various substitutions, alterations, and/or modifications, including but not limited to those specifically discussed herein, may be made to the disclosed embodiment of the invention without departing from the spirit and scope of the invention as defined in the appended claims, which follow.

What is claimed is:

1. A medical electrical lead comprising a lead body having a first section and a second section, the first section connected to the second section by a third section having a bend, the third section is less flexible than either the first section or the second section further characterized in that:

the third section has a straight leg portion located proximal to the bend, a first electrode positioned along the straight leg portion, and a tine member mounted to the third section, the tine member extending away from the lead body, a second electrode mounted to the tine member.

2. The medical electrical lead according to claim 1 wherein the second electrode is mounted to a distal end of the tine member.

3. The medical electrical lead according to claim 1 wherein the radius of the bend is between 12.5 mm–13.5 mm.

4. The medical electrical lead according to claim 3 wherein the radius of the bend is 13 mm.

5. The medical electrical lead according to claim 1 wherein the second section is less flexible than the first section.

6. The medical electrical lead according to claim 1 wherein the bend is between 135 and 45 degrees.

7. The medical electrical lead according to claim 6 wherein the bend is 90 degrees.

8. The medical electrical lead according to claim 2 wherein the second electrode is hemispherical.

9. The medical electrical lead according to claim 1 wherein the intermediate section further having a distal straight leg portion located distal to the bend.

10. The medical electrical lead according to claim 1 wherein the first electrode has a porous platinized surface.

11. A lead in accordance with claim 10 wherein the first electrode has a monolithic controlled release device.

12. An electrode assembly in accordance with claim 11 wherein the first electrode has a drug-elution port.

13. An electrode assembly in accordance with claim 1 wherein a distal end of the first section has an electrode.

14. A body-implantable medical electrical lead comprising:

a lead body having a straight distal section, an intermediate section and a straight proximal section, the proximal section more flexible than the distal section, the distal section being more flexible than the intermediate section;

a first electrode positioned proximal to the straight distal section, and a second electrode positioned on the distal section.

15. The medical electrical lead according to claim 14 wherein the intermediate section has a curved portion.

16. The medical electrical lead according to claim 15 wherein the curved portion curves between 135 and 45 degrees.

17. The medical electrical lead according to claim 16 wherein the curved portion curves 90 degrees.

18. The medical electrical lead according to claim 15 wherein the curved portion has a proximal straight leg portion attached to a proximal end of the curved portion and a distal straight leg portion attached to a distal end of the curved portion.

19. The medical electrical lead according to claim 18 wherein the first electrode is positioned on the proximal straight leg section of the curved portion.

20. The medical electrical lead according to claim 19 wherein the first electrode has a porous platinized surface.

21. A medical electrical lead in accordance with claim 14 further comprising a tine member mounted to the intermediate section, the tine member extending away from the lead body, a second electrode mounted to the tine member.

22. A medical electrical lead comprising:

a lead body having a relatively straight first section and a relatively straight second section, the relatively straight first section connected to the relatively straight second section by a third section having a bend, the third section is less flexible than either the first section or the second section, the third section having a tine extending therefrom;

a first electrode positioned on the tine extending from the third section; and a second electrode positioned on the second section.

23. The medical electrical lead according to claim 22 wherein the tine has a tine outer radius, the first electrode has a first electrode outer radius, the first electrode outer radius being greater than the tine outer radius such that the first electrode overhangs the tine by a first amount.

24. The medical electrical lead according to claim 23 wherein the first electrode overhangs the tine by a first amount which is an amount between 0.010 cm–1.000 cm.

25. The medical electrical lead according to claim 22 wherein the first amount is 0.020 cm.

26. The medical electrical lead according to claim 22 wherein the first electrode comprises a bipolar electrode.

27. The medical electrical lead according to claim 22 wherein the radius of the bend is between 12.5 mm –13.5 mm.

28. The medical electrical lead according to claim 27 wherein the radius of the bend is 13 mm.

29. The medical electrical lead according to claim 22 wherein the second section is less flexible than the first section.

30. The medical electrical lead according to claim 22 wherein the bend is between 135 and 45 degrees.

31. The medical electrical lead according to claim 30 wherein the bend is 90 degrees.

32. A body-implantable medical electrical lead comprising:
- a lead body having a straight distal section, an intermediate section and a straight proximal section, the proximal section more flexible than the distal section, the distal section being more flexible than the intermediate section;
- a first electrode positioned proximal to the distal section, and
- a second electrode positioned on the distal section.

33. The medical electrical lead according to claim 32 wherein the intermediate section has a bend.

34. The medical electrical lead according to claim 32 wherein the bend is between 135 and 45 degrees.

35. The medical electrical lead according to claim 34 wherein the bend is 90 degrees.

36. The medical electrical lead according to claim 33 wherein the bend on intermediate section is on a curved portion, the intermediate section further having a proximal straight leg portion attached to a proximal end of the curved portion and a distal straight leg portion attached to a distal end of the curved portion.

37. The medical electrical lead according to claim 36 wherein the first electrode is positioned on the proximal straight leg section of the curved portion.

38. The medical electrical lead according to claim 37 wherein the atrial electrode comprises a first electrode and a second electrode.

39. The medical electrical lead according to claim 38 wherein the first electrode has a porous platinized surface.

40. A lead in accordance with claim 38 wherein the first electrode assembly has a monolithic controlled release device.

41. An electrode assembly in accordance with claim 37 wherein the atrial electrode has a drug-elution port.

42. A medical electrical lead comprising:
- a lead body having a relatively straight first section and a relatively straight second section, the relatively straight first section connected to the relatively straight second section by a third section, the third section is less flexible than either the first section or the second section; the third section having a straight proximal section, a bent middle section and a straight distal section; a tine extending away from the third section;
- a first electrode positioned on the tine; and
- a second electrode positioned on the second section.

43. The medical electrical lead according to claim 42 wherein the first section is between 302–327 mm.

44. The medical electrical lead according to claim 42 wherein the second section is approximately 90 mm.

45. The medical electrical lead according to claim 42 wherein the bend of the third section is between 12.5 mm–13.5 mm.

46. The medical electrical lead according to claim 42 wherein the bent middle section has a bend radius of 13 mm.

47. The medical electrical lead according to claim 42 wherein the bend is between 135 and 45 degrees.

48. The medical electrical lead according to claim 42 wherein the bent middle section has a bend of 90 degrees.

49. The medical electrical lead according to claim 42 wherein the straight proximal section of the third section is 38.5 mm–39.5 mm.

50. The medical electrical lead according to claim 42 wherein the straight distal section of the third section is 9.5 mm–10.5 mm.

51. The medical electrical lead according to claim 42 wherein the second section is less flexible than the first section.

* * * * *

UNITED STATES PATENT AND TRADEMARK OFFICE
CERTIFICATE OF CORRECTION

PATENT NO.   : 6,006,139
DATED        : December 21, 1999
INVENTOR(S)  : Kruse et al.

Page 1 of 1

It is certified that error appears in the above-identified patent and that said Letters Patent is hereby corrected as shown below:

<u>Title page,</u>
Item [57], ABSTRACT,
Line 2, change "lead features a" to -- lead feature a --.

Signed and Sealed this

Eighteenth Day of March, 2003

JAMES E. ROGAN
*Director of the United States Patent and Trademark Office*